(12) United States Patent
Botto et al.

(10) Patent No.: US 9,320,703 B2
(45) Date of Patent: Apr. 26, 2016

(54) EXTRACT OF COTTON FIBERS AND COSMETIC COMPOSITION AND USE THEREOF FOR PROTECTING, NOURISHING AND HYDRATING THE SKIN

(71) Applicant: ISP Investments Inc., Wilmington (DE)

(72) Inventors: Jean-Marie Botto, Garbejaire (FR); Nouha Domloge, Valbonne (GB); Frederique Portolan, Valbonne (FR)

(73) Assignee: ISP INVESTMENTS INC., Wilmington, DE (US)

( * ) Notice: Subject to any disclaimer, the term of this patent is extended or adjusted under 35 U.S.C. 154(b) by 0 days.

(21) Appl. No.: 14/406,930

(22) PCT Filed: Jun. 6, 2013

(86) PCT No.: PCT/FR2013/051298
§ 371 (c)(1),
(2) Date: Dec. 10, 2014

(87) PCT Pub. No.: WO2013/186465
PCT Pub. Date: Dec. 19, 2013

(65) Prior Publication Data
US 2015/0164779 A1    Jun. 18, 2015

(30) Foreign Application Priority Data

Jun. 11, 2012   (FR) ...................................... 12 01664

(51) Int. Cl.
| | | |
|---|---|---|
| *A61K 8/97* | (2006.01) | |
| *A61K 8/60* | (2006.01) | |
| *A61Q 5/00* | (2006.01) | |
| *A61Q 19/00* | (2006.01) | |
| *A61K 8/34* | (2006.01) | |
| *A61Q 17/00* | (2006.01) | |

(52) U.S. Cl.
CPC . *A61K 8/97* (2013.01); *A61K 8/345* (2013.01); *A61K 8/60* (2013.01); *A61K 8/602* (2013.01); *A61Q 5/00* (2013.01); *A61Q 17/00* (2013.01); *A61Q 19/00* (2013.01); *A61Q 19/007* (2013.01)

(58) Field of Classification Search
None
See application file for complete search history.

(56) References Cited

U.S. PATENT DOCUMENTS

| | | | | |
|---|---|---|---|---|
| 4,427,778 | A | * | 1/1984 | Zabriskie ...................... 435/277 |
| 4,490,361 | A | * | 12/1984 | Heldebrant ................... 530/383 |
| 4,787,980 | A | * | 11/1988 | Ackermann et al. .......... 210/638 |
| 5,466,441 | A | | 11/1995 | Fisher et al. |
| 5,780,046 | A | * | 7/1998 | Humber et al. ............... 424/440 |
| 6,265,207 | B1 | * | 7/2001 | Cox .............................. 435/263 |
| 7,413,755 | B2 | | 8/2008 | Dal Farra et al. |
| 2003/0138484 | A1 | * | 7/2003 | Gianesello et al. ........... 424/465 |
| 2004/0062739 | A1 | | 4/2004 | Mehul |
| 2006/0018868 | A1 | | 1/2006 | Dal Farra et al. |
| 2006/0165632 | A1 | | 7/2006 | Mehul |
| 2007/0207108 | A1 | * | 9/2007 | Yamasaki et al. .......... 424/70.13 |
| 2008/0175904 | A1 | * | 7/2008 | Mathiesen et al. ............ 424/464 |
| 2009/0232892 | A1 | | 9/2009 | Yamasaki et al. |
| 2011/0064832 | A1 | | 3/2011 | Burke-Colvin et al. |
| 2011/0223223 | A1 | * | 9/2011 | Murata et al. ................. 424/401 |
| 2012/0015064 | A1 | | 1/2012 | Burke-Colvin et al. |

FOREIGN PATENT DOCUMENTS

| | | |
|---|---|---|
| DE | 2020080140068 | 9/2009 |
| EP | 1179339 | 2/2002 |
| EP | 1930012 | 6/2008 |
| FR | 2799647 | 4/2001 |
| FR | 2847815 | 6/2004 |
| FR | 2947727 | 1/2011 |
| JP | 2008/001599 | 1/2008 |
| WO | 02/38110 | 5/2002 |
| WO | 2004/052331 | 6/2004 |
| WO | 2011/026039 | 3/2011 |

OTHER PUBLICATIONS

PCT, International Search Report, International Application No. PCT/FR2013/051298 (Aug. 14, 2013).

* cited by examiner

*Primary Examiner* — Jennifer Berrios
(74) *Attorney, Agent, or Firm* — Thompson Hine LLP

(57) ABSTRACT

The invention relates to an extract of cotton fibers, a cosmetic composition comprising, by way of an active principle, at least one extract of cotton fibers, formed by mono, di, tri and tetra saccharides, in a physiologically suitable medium. The invention also relates to a cosmetic treatment method for protecting keratin substrates, for reinforcing the skin's cutaneous barrier and/or for reinforcing protection of the hair and/or for enhancing keratin synthesis and/or for nourishing keratin substrates. The invention also relates to a method for producing an extract of cotton fibers and to the use thereof for the preparation of a cosmetic composition according to the invention.

6 Claims, 1 Drawing Sheet

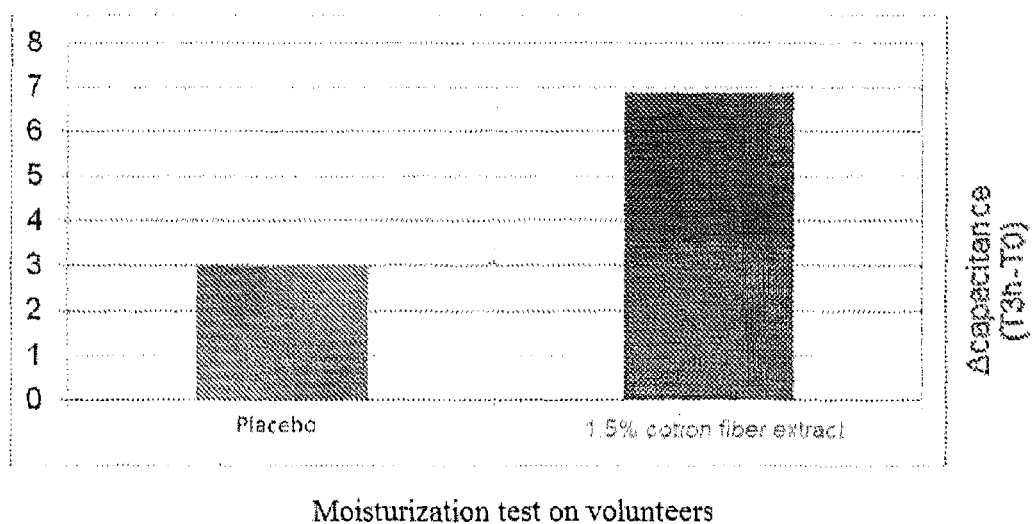
Moisturization test on volunteers

EXTRACT OF COTTON FIBERS AND COSMETIC COMPOSITION AND USE THEREOF FOR PROTECTING, NOURISHING AND HYDRATING THE SKIN

The invention relates to the field of cosmetics.

The present invention relates to a cotton fibers extract comprising a cotton fibers hydrolysate constituted of mono, di, tri and tetra-saccharides, and a cosmetic composition comprising as an active agent, in a physiologically acceptable medium, at least one cotton fibers extract.

The skin is the main keratin substrate in the organism. It is a vital organ covering the entire surface of the body and carrying out multiple functions such as sensory functions, protective functions against multiple external attacks, immune, metabolic or heat-regulating functions. These roles are enabled due to a complex structure associating varied tissue structures.

The skin is constituted of three separate overlaid compartments: the epidermis, the dermis and the hypodermis. The epidermis is an epithelial coating forming the outer structure of the skin and provides the protective function thereof. This function is provided by epithelial cell cohesion and by the production of a resistant filamentous protein: keratin. The epidermis is characterized by an organization in strata corresponding to an increasing state of keratinocyte differentiation, from the deepest region (stratum basale) to the uppermost region (stratum corneum). During the migrations thereof to the surface, the keratinocytes are flattened and the synthesis of keratins, a family of fibrous proteins, intensifies. While progressing to the upper layers, the keratinocytes are flattened further, the nucleus thereof starts to degenerate. The cell content rich in lipids, cholesterol, saturated free fatty acids and ceramides, is then excreted into the extracellular space, increasing the cohesion between the cells and contributing to the barrier role of the epidermis.

The stratum corneum is thus very resistant to external attacks. Keratin is the essential composition of all keratin substrates and in particular capillary fibers, body hair, nails and other skin appendages.

Hair on the head, or body, is a capillary structure constituted of dead cells filled with keratin filaments and lipid residues from plasmic membranes. Each hair is produced by a hair follicle, in turn constituted of a bulb, a hair shaft and a sebaceous gland. In the bulb, the keratinocytes situated at the periphery form the proliferation site. During differentiation, the keratinocytes move toward the center of the follicle to form the hair shaft and are filled with keratin fibers, rendering the hair very resistant.

For many years, health and cosmetics professionals have been seeking means for the care of keratin substrates, particularly the skin and hair, and means for increasing the resistance of the skin and hair to external attacks and to the stress to which they are subjected on a daily basis.

A number of substances introduced into cosmetic or pharmaceutical products have emerged, but there remains a need to develop novel ingredients for protecting keratin substrates, reinforcing the skin barrier and limiting the impact of external attacks. Moreover, the inventors set themselves the objective of developing a plant-based cosmetic production, so as to meet the expectations of consumers and increasing requirements in respect of safety.

The technical problem to solve was thus, for the inventors, that of finding a, physiologically acceptable, novel plant-based product, which is capable of providing genuine care for keratin substrates, but also of protecting skin and hair effectively so that they are not subject to the damage caused by external attacks and stress.

The inventors succeeded in selecting a plant-based natural product which, suitably treated, has remarkable properties when applied to a keratin substrate. Unexpectedly, the inventors discovered that a cotton fibers extract comprising a cotton fibers hydrolysate constituted exclusively of mono, di, tri and tetra-saccharides has remarkable properties in respect of keratin substrates and, in particularly, that it protects skin and hair.

Cotton is the set of fibers (or hairs) covering the seed of the cotton plant. The cotton plant, or *Gossypium*, is a dicotyledon of the Malvaceae family. There are 40 to 50 known perennial or annual, ligneous or herbaceous species. Only four thereof are cultivated for the fiber thereof: *Gossypium hirsutum*, *Gossypium barbadense*, *Gossypium herbaceum* and *Gossypium arboreum*. These four cotton plant species have given rise to numerous hybrid varieties, classified according to the length of the fiber thereof, seed pubescence and bract shape. The *Gossypium hirsutum* cotton plant line alone supplies 80 to 90% of worldwide cotton production. The fruit of the cotton plant is a coarse oval capsule, containing very numerous seeds bearing close hairs (or fibers) of varied lengths. Using these fibers, suitably treated, the inventors developed the novel cotton fibers extract and the cosmetic composition according to the invention.

To the applicant's knowledge, the use of a product based on hydrolyzed cotton fibers in cosmetic compositions has never been described in the prior art. To date, only cotton seed oils and cotton fibers have been used in cosmetics, such as for example in the U.S. Pat. No. 5,466,441 or in the patent FR2799647.

The patent FR2799647 discloses compositions in emulsion form containing fibers, at least one silicone surfactant and at least one wax, for the treatment, protection, care, makeup removal and/or cleansing of skin, lips and/or hair. Cotton fibers are cited without being exemplified, or preferred. The preferred fibers are synthetic and have a length between 0.1 and 1.5 mm.

Compositions based on cotton honeydew are also disclosed in the patent application WO2004052331 for treating keratin substrates, said cotton honeydew being a substance secreted by insects and found on cotton. It essentially contains sugars synthesized by insects and sugars of physiological origin, particularly glucose, fructose, saccharose, trehalose, melezitose and inositol.

Thus, according to a first aspect, the present invention relates to a cotton fibers extract comprising a cotton fibers hydrolysate constituted exclusively of monosaccharides and/or disaccharides and/or trisaccharides and/or tetrasaccharides.

The term "cotton fibers hydrolysate" according to the present invention denotes a product resulting from the hydrolysis of cotton fibers via an enzyme reaction, particularly a cellulase.

The term "cotton fibers extract" according to the present invention denotes an aqueous solution comprising an enzymatically hydrolyzed cotton fibers extract produced according to the method described hereinafter.

The term "saccharides" according to the present invention denotes any carbohydrates which are a class of organic molecules containing a carbonyl group (aldehyde or ketone) and a plurality of hydroxyl (—OH) groups. Particular reference is made to any carbohydrates comprising six carbon atoms.

The term "monosaccharides and/or disaccharides and/or trisaccharides and/or tetrasaccharides" according to the present invention denotes any saccharides comprising one saccharide or two, three or four saccharides bound together.

The cotton fibers extract comprises a cotton fibers hydrolysate hydrolyzed enzymatically according to the method described hereinafter.

In one preferred embodiment of the cotton fibers extract according to the invention, the monosaccharides, disaccharides, trisaccharides and/or tetrasaccharides are glucose, cellobiose, cellotriose, cellotetraose and cellulose oligomers.

In one particularly preferred embodiment according to the invention, the cotton fibers extract further comprises at least one additional saccharide. The saccharide(s) are preferably of natural origin, and preferably glucose and/or fructose and/or trehalose and/or saccharose and/or inositol.

The cotton fibers extract advantageously further comprises the following additional saccharides: glucose, fructose, trehalose, saccharose and inositol.

Even more advantageously, the cotton fibers extract according to the invention comprises about 2% of cotton fibers hydrolysate, 0.8% of glucose, 0.8% of fructose, 1.1% of trehalose, 1.7% of saccharose and 0.5% of inositol.

According to a second aspect, the present invention relates to a cosmetic composition comprising as an active agent, in a physiologically acceptable medium, a cotton fibers extract as described hereinafter.

The term "a physiologically acceptable medium" denotes a medium compatible with skin or hair on the head or body.

The cosmetic composition according to the invention comprises as an active agent, a natural plant-based product, the cotton fibers extract, which has been hydrolyzed enzymatically according to the method described hereinafter. The inventors demonstrated, surprisingly, that cosmetic compositions comprising as an active agent a cotton fibers extract according to the invention, particularly make it possible to protect cells against osmotic shocks, to obtain protection against damage caused to cell deoxyribonucleic acid (DNA), particularly that the cosmetic compositions make it possible to protect cell DNA when said cells are subject to stress such as, for example, nutrient deprivation. Thus, the inventors demonstrated that the cosmetic compositions have a protective effect on keratinocytes and on DNA and are particularly suitable for moisturizing skin.

These protective properties of the cosmetic compositions according to the invention may be used, for example for protecting skin and/or hair against external attacks caused, in particular, by the action of sunrays or by further physical, chemical or biological agents. These protective properties may also be used for combating skin aging.

It is obvious that the active agent according to the invention may be used alone or in association with further active agents.

According to the invention, it is possible to add to the cosmetic composition according to the invention further active agents particularly intended for preventing and/or treating skin signs of aging and/or protecting skin and/or hair against external attacks.

Thus, the cosmetic compositions suitable for use according to the invention may further contain at least one further active agent for boosting the action of the cotton fibers extract according to the invention, in the field of the prevention and improvement of skin signs of aging or for extending the range of properties of the cosmetic composition according to the invention.

We can cite, in a non-limiting manner, the following ingredient classes in the field of cosmetics: regenerating, anti-age, anti-wrinkle, soothing, antioxidant, healing, relipidizing, nourishing, anti-radical, anti-glycation, moisturizing, anti-bacterial, antifungal, keratolytic, muscle relaxant, desquamation, firming agents, dermal macromolecule synthesis or energy metabolism or microcirculation or nail growth or hair growth stimulating agents, epidermal differentiation or pigmentation modulating agents, metalloproteinase inhibiting agents or sun filters.

In a more particular embodiment, the cosmetic composition according to the invention will comprise, besides the cotton fibers extract according to the invention, at least one cytochrome c activating compound and/or, at least one moisturizing compound, such as an aquaporin activating compound and/or, at least one sirtuin activating compound and/or, at least one compound increasing cell adhesion and/or, at least one compound increasing the production of matrix proteins such as collagen, fibronectin, laminin, glycosaminoglycans and/or, at least one proteasome activity modulating compound and/or, at least one circadian rhythm modulating compound and/or, at least one HSP protein modulating compound and/or, at least one compound increasing cell energy and/or, at least one skin pigmentation modulating compound and/or, at least one coenzyme Q10 activating compound and/or, at least one compound enhancing the barrier function, such as a transglutiminase or HMG-CoA reductase activating compound and/or, at least one mitochondrial protection compound.

Said compounds above may be of natural origin, such as plant peptide extracts, or of synthetic origin, such as peptides.

Independently of the functions thereof, the further active agents or active substances associated with the active agent or active substance according to the invention in the composition may have very diverse chemical structures. We can cite, in a non-limiting manner, peptides, vitamin C and the derivatives thereof, group B vitamins, DHEA (dihydroepiandrosterone), phytosterols, salicylic acid and derivatives thereof, retinoids, flavonoids, sugar amines, azoles, metal salts, allantoin, peptide extracts of plant origin or polymers.

Furthermore, the cosmetic composition according to the invention may further comprise at least one compound enhancing hair health.

We can particularly cite vitamins, further plant peptide extracts, minoxidil, nicotinic acid esters, trace elements, anti-inflammatory agents, retinoic acid or derivatives thereof, retinol, 5α-reductase inhibitors or peptide compounds derived from chemical synthesis. By way of examples of vitamins, mention may be made of vitamins A, E, B5, B6, C, H, or PP, by way of examples of trace elements, mention may be made of zinc, copper, magnesium, or silicon.

According to one advantageous embodiment of the invention, the cotton fibers extract is present in the cosmetic composition at a concentration between 0.01% and 20% by weight with respect to the total weight of the composition, and preferentially at a concentration between 0.1% and 10% by weight with respect to the total weight of the composition.

According to one particularly advantageous embodiment of the invention, the cosmetic composition according to the invention also comprises between 0.01% and 5% by weight with respect to the total weight of the composition of at least one additional saccharide such as glucose and/or fructose and/or trehalose and/or saccharose and/or inositol.

The term "at least one additional saccharide" according to the present invention infers that the active agent, in addition to the monosaccharides and/or disaccharides and/or trisaccharides and/or tetrasaccharides, comprises saccharides added to the composition initially obtained by enzymatic hydrolysis of the cotton fibers. These saccharides are preferentially glucose and/or fructose and/or trehalose and/or saccharose and/or inositol.

In a further more advantageous embodiment of the invention, the cosmetic composition according to the invention comprises about 2% of cotton fibers extract, 0.8% of glucose, 0.8% of fructose, 1.1% of trehalose, 1.7% of saccharose and 0.5% of inositol.

The cosmetic compositions according to the present invention are intended for the care of keratin substrates.

In the invention, the expression "keratin substrate" denotes any substrates mainly composed of keratin. These are substrates such as skin, hair, eyelashes, eyebrows or nails or skin appendages in general. The term care of keratin substrates denotes any actions intended to conserve or restore proper functioning of this substrate, or any means for conserving or enhancing the appearance thereof. Thus, care includes moisturization, soothing, protection against any types of attacks, particularly sun protection, combating and preventing signs of aging, particularly skin signs of aging.

The term "skin signs of aging" denotes any modifications of the external appearance caused by aging such as, for example, wrinkles and lines, wizened skin, soft skin, thinned skin, lack of skin suppleness and/or tone, lackluster and dull skin but also any internal modifications of skin not systematically conveyed by a modified external appearance such as, for example any internal skin damage following exposure to ultraviolet radiation.

For cleansing and/or washing hair and/or skin, the use of detergent lotions (such as shampoos and other soaps) essentially based on conventional surfactant agents particularly of the anionic, non-anionic and/or amphoteric type, but more particularly of the anionic type, is routine. These compositions are applied to moistened keratin substrates and the foam generated by rubbing makes it possible, after rinsing with water, to remove the various types of dirt initially present. These compositions may have a good washing power but the cosmetic properties associated therewith remain however relatively poor in view of the relatively aggressive nature of such a cleansing treatment. Indeed, this treatment may, in the long term, causes more or less marked damage on the hair fibers and/or on the skin, particularly linked with progressive elimination of the proteins contained in or on the surface thereof. Thus, in order to enhance the cosmetic properties of the detergent compositions above, one solution is that of introducing supplementary cosmetic agents essentially intended to repair or limit the harmful or adverse effects induced by the various treatments or attacks to which the hair fibers and skin are subjected, i.e. to protect. These cosmetic agents may be, for example, a cotton fibers extract according to the invention or a cosmetic composition according to the invention.

The cosmetic compositions according to the invention are intended to enhance the appearance and quality of the keratin substrates of the user thereof.

The cosmetic compositions according to the present invention are presented in a dosage form suitable for cutaneous topical administration and suitable for administration on hair. It covers all cosmetic forms. These compositions should thus contain a physiologically acceptable medium, i.e. compatible with skin or hair on the head or body. These compositions may particularly be presented in the form of an aqueous, hydro-alcoholic or oil-based solution; an oil-in-water, water-in-oil emulsion or multiple emulsions; they may also be presented in the form of creams, suspensions or powders, suitable for application on the skin, mucosa, lips and/or hair.

These compositions may be more or less fluid and have the appearance of a cream, lotion, milk, serum, ointment, shampoo, gel, paste or foam. They may also be presented in solid form, such as a stick or applied to the skin in aerosol form. They may be used as a skin care and/or makeup product.

These compositions further comprise any additive routinely used in the envisaged field of application and the adjuvants required for the formulation thereof, such as solvents, thickeners, diluents, antioxidants, colorants, sun filters, self-tanning agents, pigments, fillers, preservatives, fragrances, odor absorbers, cosmetic agents, essential oils, vitamins, essential fatty acids, surfactants, film-forming polymers, etc. In any case, those skilled in the art will ensure that these adjuvants and the proportions thereof are chosen so as not to impair the sought advantageous properties of the cosmetic composition according to the invention. These adjuvants may, for example, be present at a concentration of 0.01 to 20% of the total weight of the composition.

When the cosmetic composition according to the invention is an emulsion, the fatty phase may represent 5 to 80% by weight and preferably 5 to 50% by weight with respect to the total weight of the composition. The emulsifiers and co-emulsifiers used in the composition will be chosen from those conventionally used in the field in question. For example, they may be used in a proportion ranging from 0.3 to 30% by weight, with respect to the total weight of the composition. Obviously, those skilled in the art will take care to choose any active or inactive supplementary compounds, and/or the quantities thereof, such that the advantageous properties of the mixture are not or are substantially not impaired by the envisaged addition.

The compositions according to the invention are applicable particularly as a cosmetic composition for skin, mucosa and/or semimucosa, but also as a cosmetic composition for hair on the head and/or body. It is also possible to envisage an application in the field of facial and body skin makeup compositions, such as lipsticks, foundations, tinted creams, under-eye concealer sticks, sunscreen or artificial tanning compositions.

The compositions according to the invention are applicable in a large number of cosmetic applications, particularly for the treatment, protection, care, makeup removal and/or cleansing of skin, lips and/or hair, and for makeup for skin, lips, eyelashes and/or the body.

The cosmetic compositions according to the invention may also consist of solid preparations also comprising soaps or cleansing cakes.

The cosmetic compositions may be also packaged in the form of a composition for aerosol also comprising a pressurized propellant. The compositions may be also for oral use, for example toothpaste.

The cosmetic composition according to the invention may be intended to form a protective filter on keratin substrates.

The invention thirdly relates to a cosmetic treatment method for protecting keratin substrates, and more particularly for protecting skin and hair, against any types of external attacks consisting of applying on the surface of the keratin substrates, and more particularly on skin and/or hair, an effective quantity of a cosmetic composition according to the invention.

The invention also relates to a cosmetic treatment method for reinforcing the skin barrier and/or reinforcing hair protection and/or for increasing keratin synthesis and/or for nourishing keratin substrates, and more particularly the skin and hair, consisting of applying on the surface of the skin and/or hair, an effective quantity of a cosmetic composition according to the invention.

The invention fourthly relates to a method for preparing a cotton fibers extract comprising the following steps:

a—cotton fibers reduced to powder are stirred in osmosed water in the presence of cellulases, b—the hydrolysis is performed for a time between 15 and 24 hours at a temperature of about 50° C., to obtain a cotton fibers hydrolysate c—the cellulases are deactivated by heating to 80° C. for about two hours, d—the hydrolysate obtained is filtered optionally concentrated or diluted in osmosed water and glycerol.

According to one particular embodiment of the invention, the hydrolysis step b is performed for a time of about 18 hours.

According to the method for preparing a cotton fibers extract according to the invention, it is performed in the steps described hereinafter:

The cotton fibers (*Gossypium* genus, preferentially *Gossypium hirsutum, Gossypium herbaceum*, and more preferentially *Gossypium hirsutum*) are reduced to powder. Alternatively, raw fibers pretreated with a 14% soda solution for at least 12 hours may be used.

A proportion by weight of 10 to 20% of fibers is placed under stirring in the presence of water (10% min-20% max), and then subjected to enzymatic hydrolysis by cellulases.

The enzymes are then deactivated by heating.

The mixture is filtered, concentrated or diluted to obtain a concentration between 20 and 50 g/kg of saccharides such as monosaccharides and/or disaccharides and/or trisaccharides and/or tetrasaccharides and more particularly glucose and/or cellobiose and/or cellotriose and/or cellotetraose and/or cellulose oligomers.

About 30% by weight of glycerol is added.

The mixture is filtered by filtering on plates of decreasing porosity to 0.2 μm and pasteurized at a low temperature.

In one particular embodiment according to the invention, one or a plurality of pure sugars (saccharides), of plant origin may be added, prior to the filtration step in the proportions specified hereinafter:

| | |
|---|---|
| Glucose | 0.5-1.5% |
| Fructose | 0.5-1.5% |
| Trehalose | 1.0-1.5% |
| Saccharose | 1.5-2.5% |
| Inositol | 0.3-0.7% |

The final total sugar concentration of the cotton fibers extract, optionally supplemented with sugars, is between 55 and 75 g/kg.

The invention fifthly relates to the use of a cotton fibers extract obtained according to the preparation method described above for preparing a cosmetic composition according to the invention.

The present invention will now be illustrated using the following examples, which shall not limit the scope of the present invention.

EXAMPLE 1

Method for Preparing the Cotton Fibers Extract 14.3 kg of cotton fibers (*Gossypium hirsutum* species) reduced to powder are placed under stirring in up to 100 kg of osmosed water in the presence of 1.15 kg of cellulase type enzyme, i.e. (CELLUCLAST®CL).

Hydrolysis is performed while maintaining this mixture for 18 hours at 50° C. The enzymes are then deactivated by heating to 80° C. for 2 hours and the mixture is filtered (Standard filtration step, preferentially bell filter).

At this stage, the extract contains only sugars, at a concentration of 40 g/kg of total sugars. The total sugar assay is performed using the sugar-phenol technique.

This extract is then filtered and diluted to obtain a final concentration of 20 g/kg of total sugars.

The thin layer chromatography analysis demonstrates that the extract contains monosaccharides, disaccharides, trisaccharides and tetrasaccharides and more particularly glucose, cellobiose, cellotrioses, cellotetraose and cellulose oligomers.

The extract is diluted in a mixture of osmosed water and 30% glycerol so as to obtain a total sugar concentration of 20 g/kg.

The mixture is filtered by filtering on plates of decreasing porosity to 0.2 μm and pasteurized at a low temperature.

The following sugars are added:

| | |
|---|---|
| Glucose | (0.8%) |
| Fructose | (0.8%) |
| Trehalose | (1.1%) |
| Saccharose | (1.7%) |
| Inositol | (0.5%) |

The final concentration of the extract of 60 g/kg of total sugars.

EXAMPLE 2

Demonstration of the Effect of Cotton Fibers Extract on Keratin Synthesis

The experiments were conducted on human skin sections placed in culture for 24 hours. The keratin expression was studied, on these skin sections, using the immunofluorescence labeling method.

The cotton fibers extract prepared in example 1 was diluted in a "phosphate buffer saline" (PBS) buffer to obtain a final concentration of 0.5% and the dilution was then applied to the skin sections, at a rate of two applications. The effect of the extract was evaluated by comparing with a skin section not treated with the cotton fibers extract according to the invention.

After application, the skin samples were cultured for 24 hours, and then prepared for inclusion in paraffin. Immunolabeling was then carried out using an anti-keratin antibody. The quantity of keratin was detected by immunofluorescence.

These studies demonstrated a marked increase in keratin fluorescence on the skin sections treated with the cotton fibers extract compared to the untreated sections. These results show a significant increase in keratin synthesis.

EXAMPLE 3

Demonstration of the Protective Effect of Cotton Fibers Extract on Keratinocytes The study was conducted on HaCaT human keratinocytes, in the exponential growth phase in Labtecks™. The keratinocytes were inoculated in 96-well plates.

Cells are pretreated for 2 hours in the presence of 0.5% extract. The control condition applied is constituted of cells not treated with the extract according to the invention. Then, the culture medium, containing or not containing the extract, is replaced by PBS for a 3 hour period.

Cell viability tests were conducted using the MTT test. As a general rule, the MTT agent is used to assess the cytotoxicity of a product with respect to a cell medium by measuring cell viability.

The keratinocytes are incubated in a solution containing 0.1 mg/ml of MTT (3-[4,5-dimethylthiazol-2-yl]-2,5-diphenyltetrazolium bromide). This compound is absorbed by the live cells and metabolized by mitochondrial enzymes (succinate dehydrogenase) into a violet blue compound, formazan, presented in the form of violet crystals insoluble in aqueous media.

The formazan crystals are solubilized in DMSO, they give an optical density (O.D.) proportional to the number of live cells present in the sample. Optical density measurements were then conducted for each sample studied (with the O.D. read at 540 nm). The O.D. is then directly proportional to the enzyme activity and to the number of live cells.

The results demonstrated that the cells cultured in PBS, i.e. completely deprived of nutrients, are subject to very intense stress and are rapidly altered.

Similarly, these measurements demonstrated that, according to the extract concentrations used, the cells treated with said extract have a viability increasing from 15% to 30% compared to the untreated cells. These results thus clearly demonstrate that the cotton fibers extract according to the invention has a significant cellular protection potential.

EXAMPLE 4

Demonstration of the Protective Effect of Cotton Fibers Extract Against Osmotic Shock The study was conducted on HaCaT human keratinocytes, in the exponential growth phase in Labtecks™. The cells were then treated for 1 hour in the presence of 0.5% cotton fibers extract. The medium was then removed and the keratinocytes were incubated for 1 hour in a hypertonic medium (i.e. containing DMEM and 500 mM of NaCl).

An MTT test (as described above) was then conducted in order to study the cell viability.

The result of this test demonstrates that the cell viability is reduced by half when said cells are subject to osmotic shock. Furthermore, the results demonstrate that pretreating with cotton fibers extract increases keratinocyte viability by 32% compared to the control cells, i.e. not treated with the extract but subjected to osmotic shock.

EXAMPLE 5

Demonstration of the Effect of Cotton Fibers Extract on DNA Protection

The same test as that in example 3 was performed: the cells were subjected to stress induced by nutrient deprivation ("food starvation").

Following this stress, a comet assay was conducted in order to assess the DNA degradation of the cells treated with cotton fibers extract compared to the cells not treated with the extract.

The comet assay or "Single Cell Gel Electrophoresis" is a rapid agarose microgel electrophoresis technique for viewing single and double-stranded DNA breaks on individual cells.

After treatment, the cells are confined in an agarose gel and lyzed in a high salinity buffer containing detergents. The DNA is then denatured with an alkaline bath followed by brief electrophoresis, and is then detected using propidium iodide. The DNA of an altered cell is stretched toward the anode in proportion to the number of breaks, adopting the approximate shape of a comet. Highly degraded DNA is found in the "tail" of the comet. An intact cell remains round, the DNA remaining compacted at the "head" of the comet.

The DNA damage is assessed using software for determining the percentage of DNA degradation.

The results demonstrate that the cells subjected to nutrient deprivation are subject to stress and the DNA thereof is degraded. Furthermore, the results demonstrate that the protection of the DNA of the cells treated with cotton fibers extract is increased by 45% compared to the control cells (i.e. the cells not treated with the extract but subjected to stress). The cotton fibers extract thus plays a significant role in DNA protection.

EXAMPLE 6

Moisturization Test on Volunteers (Clinical Test)

The study was conducted on 8 volunteers, aged from 21 to 39 years, double-blind versus placebo.

The cotton fibers extract according to example 1 was administered topically, 1.5% in a standard cosmetic formulation to obtain a cosmetic composition. A single application was carried out by an expert.

The evaluations were conducted at the times 0 and 3 hours.

The skin was observed using a non-invasive technique, using a VIVASCOPE® confocal microscope.

The quantitatively evaluated criteria were the thickness of the stratum corneum and the thickness of the stratum *granulosum*.

Result: A significant decrease in the thickness of the stratum corneum was observed after 3 hours of application of the cosmetic composition comprising the cotton fibers extract.

| Thickness of Stratum corneum | Time | % decrease | % improved volunteers |
|---|---|---|---|
| Composition with cotton fibers extract | t3 h-t0 h | −250% | 7/8 = 87.5% |

Conclusion: The decrease in the thickness of the stratum corneum is a characteristic of good moisturization and healthy appearance of skin. The compositions according to the invention thus make it possible to obtain good skin moisturization.

EXAMPLE 7

Moisturization Test on Volunteers (Second Clinical Test Protocol)

The study was conducted on 8 volunteers, aged from 21 to 39 years, double-blind versus placebo.

The cotton fibers extract according to example 1 was administered topically, 1.5% in a standard cosmetic formulation to obtain a cosmetic composition. A single application was carried out by an expert.

The evaluations were conducted at the times 0 and 3 hours.

The evaluation method used is the Corneometer CM825.

The results are shown in the graph of FIG. 1.

Results:

| Moisturization | Time | Mean | +/−sem | p | % increase | % improved volunteers |
|---|---|---|---|---|---|---|
| Placebo | t3 h-t0 h | 3.000 | 2.104 | | | |
| Composition with cotton fibers extract | t3 h-t0 h | 6.875 | 2.117 | 0.0156* | 129.16% | 6/8 = 75% | sem = standard error

Conclusions: Skin moisturization was significantly increased after 3 hours of application of the cotton fibers extract. The compositions according to the invention thus make it possible to obtain good skin moisturization.

EXAMPLE 8

Composition Preparations

| Ingredients (trade name) | Ingredients (INCI name) | % w/w | Supplier |
|---|---|---|---|
| Phase A | | | |
| Purified water | Water | 64.57 | / |
| LUBRASIL ™ II DM | Glycerin (and) Glyceryl Acrylate/Acrylic Acid Copolymer (and) Laureth-23 (and) Dimethicone | 3 | Ashland |
| Na4EDTA | Tetrasodium EDTA | 0.15 | Fischer chemical |
| LIPOXOL ® 3350 | PEG-75 | 1.5 | Sasol/IMCD |
| GLUCAM ® E-20 | Methylgluceth-20 | 3 | Unipex |
| LUBRAJEL ™ II XD Free | Glycerin (and) Glyceryl Polyacrylate | 5 | Ashland |
| SOLULAN ® C-24 Lanolin Derivative | Choleth-24 (and) Ceteth-24 | 1 | Unipex |
| LUBRAJEL ™ DV | Glycerin (and) Glyceryl Acrylate/Acrylic Acid Copolymer (and) Propylene Glycol | 3 | Ashland |
| SI-TEC ™ DMC 6038 | Bis-PEG-15 Methyl Ether Dimethicone | 3 | Ashland |
| Phase B | | | |
| ULTRAHIX ™ P100 | Acrylic Acid/VP Crosspolymer | 0.3 | Ashland |
| Phase C | | | |
| Cristalhyal | Sodium hyaluronate | 0.05 | Soliance |
| Purified water | Water | 10 | / |
| Phase D | | | |
| LRI solubilizer | PPG-26 Buteth-26 (and) PEG-40 Hydrogenated Castor Oil (and) water | 0.5 | Sensient |
| OPTIPHEN ® | Phenoxyethanol (and) Caprylyl glycol | 1.5 | Ashland |
| BESIL ® PDM 20 | Trimethylsiloxyphenyl Dimethicone | 1.5 | Wacker |
| PF Perfect smooth | Fragrance/Parfum | 0.2 | Mane |
| Phase E | | | |
| NaOH pearls | Sodium hydroxide | 0.03 | Acros/Fischer |
| Purified water | Water | 0.5 | / |

-continued

| Ingredients (trade name) | Ingredients (INCI name) | % w/w | Supplier |
|---|---|---|---|
| Phase F | | | |
| TIMIRON ® Splendid Blue | CI77891 (Titanium Dioxide) (and) Mica (and) Silica | 0.2 | Merck |
| EXTRACT according to example 1 | | 0.1 | |
| | Total | 100.00 | |

2—Oil-in-water emulsion
Oil phase:

| | | |
|---|---|---|
| MONTANOV ® 68 (Cetearyl Alcohol and Cetearyl Glucoside) | 5.00% | |
| Jojoba oil | 5.00% | |
| Petroleum jelly oil | 5.00% | |
| Isopropyl Palmitate | 7.00% | |

Aqueous Phase:

| | |
|---|---|
| Glycerin | 5.00% |
| Allantoin | 0.10% |
| EXTRACT according to example 1 | 10% |
| SEPIGEL ® 305 (Polyacrylamide and C13-14 Isoparaffin and Laureth-7) | 0.30% |
| Preservative | 0.50% |
| Fragrance | 0.50% |
| Water | q.s. 100% |

3—Gel

| | |
|---|---|
| CARBOPOL ® Ultrez 10 (2% sol.) | 25.00% |
| Triethanolamine | 0.50% |
| EXTRACT according to extract 1 | 0.5% |
| Preservative | 0.20% |
| EDTA (sequestrant) | 0.10% |
| Fragrance | 0.50% |
| Water | q.s. 100% |

4—Lotion

| | |
|---|---|
| Mono Propylene Glycol | 1.00% |
| Allantoin | 0.30% |
| Glycerin | 1.00% |
| CETIOL ® HE (PEG-7 Glyceryl Cocoate) | 1.00% |
| EXTRACT according to example 1 | 0.01% |
| Preservative | 0.20% |
| Fragrance | 0.50% |
| Water | q.s. 100% |

5—Shampoo

| | |
|---|---|
| TEXAPON ® NSO (Sodium Laureth Sulfate) | 30.00% |
| TEGOBETAINE ® HS (Cocamidopropyl Betaine) | 6.00% |
| TWEEN ™ 20 | 2.00% |
| GLUCAMATE ® DOE 120 (50% sol) | 0.75% |
| EDTA | 0.10% |
| Sodium chloride | 1.00% |
| EXTRACT according to example 1 | 0.5-1% |

-continued

| | |
|---|---|
| Preservative | 0.30% |
| Fragrance | 0.50% |
| Colorant | q.s. 100% |
| Water | q.s. 100% |
| Citric Acid | q.s. pH = 5.5-6.0 |

The invention claimed is:

1. A method for preparing a cotton fibers extract, the method comprising:
   stirring about 10% to about 20% by weight of cotton fibers in powder form in osmosed water in the presence of a cellulase,
   performing hydrolysis on the cotton fibers for a time between 15 and 24 hours at a temperature of about 50° C.,
   deactivating the cellulase by heating to about 80° C. for about two hours after performing the hydrolysis,
   filtering the mixture obtained to collect a filtrate; and
   diluting or concentrating the filtrate in osmosed water to obtain a cotton fibers extract having a concentration of about 20 g/kg to about 50 g/kg of total sugars comprising mono-, di-, tri-, and tetra-saccharides.

2. The method according to claim 1, wherein the hydrolysis is performed for a time of about 18 hours.

3. The method according to claim 1, further comprising adding, subsequent to diluting or concentrating the filtrate, additional saccharides to increase the total sugars to more than 50 g/kg.

4. The method according to claim 3, wherein said additional saccharides comprise glucose, fructose, trehalose, saccharose, and inositol.

5. The method according to claim 3, wherein said additional saccharides comprise one or more of glucose, fructose, trehalose, saccharose, and inositol.

6. The method according to claim 1, further comprising adding, subsequent to diluting or concentrating the filtrate, about 30% by weight glycerol.

* * * * *